United States Patent
Ollivier et al.

(10) Patent No.: US 8,918,192 B2
(45) Date of Patent: Dec. 23, 2014

(54) LEAD FOR IMPLANTABLE CARDIAC PROSTHESIS, INCLUDING PROTECTION AGAINST THE THERMAL EFFECTS OF MRI FIELDS

(75) Inventors: Jean-François Ollivier, Villiers-le-Bacle (FR); Philippe d'Hiver, Chatillon (FR)

(73) Assignee: Sorin CRM SAS, Clamart (FR)

( * ) Notice: Subject to any disclaimer, the term of this patent is extended or adjusted under 35 U.S.C. 154(b) by 9 days.

(21) Appl. No.: 13/545,259

(22) Filed: Jul. 10, 2012

(65) Prior Publication Data

US 2013/0018447 A1 Jan. 17, 2013

(51) Int. Cl.
| | |
|---|---|
| A61N 1/375 | (2006.01) |
| A61B 18/14 | (2006.01) |
| A61N 1/05 | (2006.01) |
| A61N 1/08 | (2006.01) |
| A61B 5/00 | (2006.01) |
| A61N 1/37 | (2006.01) |

(52) U.S. Cl.
CPC ............. *A61N 1/0565* (2013.01); *A61B 5/7203* (2013.01); *A61N 1/08* (2013.01); *A61N 1/057* (2013.01); *A61N 1/3718* (2013.01); *A61N 2001/086* (2013.01)
USPC .............................. 607/122; 606/41; 607/116

(58) Field of Classification Search
USPC .................................... 607/45, 116
See application file for complete search history.

(56) References Cited

U.S. PATENT DOCUMENTS

| | | | |
|---|---|---|---|
| 5,447,534 A | 9/1995 | Jammet | |
| 5,800,499 A | 9/1998 | Ollivier | |
| 7,123,013 B2 | 10/2006 | Gray | |
| 2003/0204217 A1 | 10/2003 | Greatbatch | |
| 2007/0233217 A1 | 10/2007 | Yang et al. | |
| 2007/0255332 A1 | 11/2007 | Cabelka et al. | |
| 2008/0154348 A1 | 6/2008 | Atalar et al. | |
| 2010/0160989 A1 | 6/2010 | Legay | |
| 2010/0160997 A1* | 6/2010 | Johnson et al. | ........... 607/45 |
| 2010/0208397 A1 | 8/2010 | Johnson et al. | |
| 2011/0054582 A1 | 3/2011 | Dabney et al. | |
| 2011/0106231 A1 | 5/2011 | Doan et al. | |

FOREIGN PATENT DOCUMENTS

| | | |
|---|---|---|
| EP | 0591053 A1 | 4/1994 |
| EP | 0779080 A1 | 6/1997 |
| EP | 0784993 A1 | 7/1997 |
| EP | 2198917 A1 | 6/2010 |

OTHER PUBLICATIONS

Foreign Search Report (Annexe Au Rapport De Recherche Preliminaire Relatif A La Demande De Brevet Francais No. FR 1156360 FA 753050) Nov. 10, 2011.

* cited by examiner

*Primary Examiner* — Carl H Layno
*Assistant Examiner* — Jon Eric C Morales
(74) *Attorney, Agent, or Firm* — Foley & Lardner LLP

(57) ABSTRACT

A lead for an implantable cardiac prosthesis, with protection against the thermal effects of MRI fields by terminating the lead head (10) with an electrically insulating tubular outer housing (28) and an anchoring mechanism. The tubular housing (28) carries an electrically isolated thermally conductive solid part in the outer region of its distal end forming a heat sink. The heat sink thermally conductive material is for example titanium, associated with an electrically insulating coating such as a diamond deposition. The anchor may be a projecting helical anchoring screw (20), axially extending the tubular housing, which is an electrically conductive active screw on at least one end portion.

16 Claims, 1 Drawing Sheet

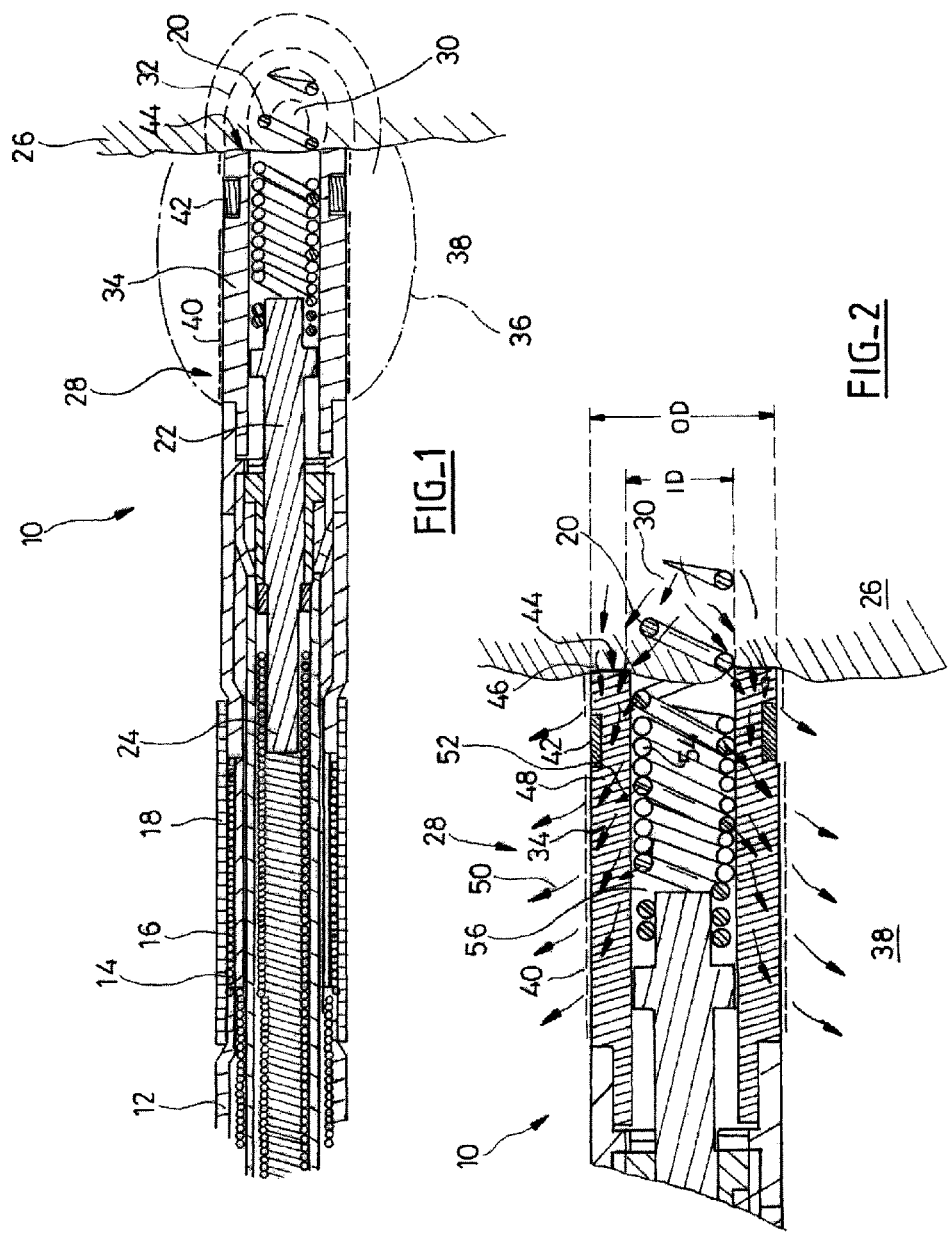

LEAD FOR IMPLANTABLE CARDIAC PROSTHESIS, INCLUDING PROTECTION AGAINST THE THERMAL EFFECTS OF MRI FIELDS

RELATED APPLICATIONS

The present application claims the benefit of French Application No. 11/56360 entitled "Lead for implantable cardiac prosthesis, comprising means for protection against the thermal effects of MRI fields" and filed Jul. 12, 2011, which is hereby incorporated by reference in its entirety.

FIELD OF THE INVENTION

The present invention relates to "active implantable medical devices" as defined by the Jun. 20, 1990 Directive 90/385/EEC of the Council of the European Communities, which includes devices that continuously monitor a patient's heart rhythm and deliver to the heart, if and as necessary, electrical stimulation pulses, for pacing, resynchronization, cardioversion and/or defibrillation, and more particularly to leads for intracardiac stimulation or defibrillation that collect (detect) depolarization signals from the patient's heart, which leads are connected to an implantable device generator, and to techniques for protecting the leads when the patient must be subjected to examination by magnetic resonance imaging (MRI).

BACKGROUND

It is known to have intracardiac leads provided at their distal end with a screw for anchoring the distal head of the lead in the tissue of the endocardium so that an electrode of the lead makes electrical contact with the patient's myocardium tissue. In addition, in the case of a lead with an "active" screw, once in place the screw itself acts as a distal electrode for detection/stimulation of the myocardium. One such screw lead, with a retractable screw, is disclosed by EP0591053A and its counterpart U.S. Pat. No. 5,447,534 (both assigned to Sorin CRM S.A.S, previously known as ELA Medical), which describes a type of lead is marketed under the brand name STELIX (registered trademark) by Sorin CRM, Clamart, France.

These leads can be endocardial leads (i.e., placed in a cavity of the myocardium in contact with the wall thereof), epicardial leads (i.e., placed on the outside of the heart, in particular to define a reference potential, or to apply a shock), or intravascular leads (i.e., introduced into the coronary sinus to a location facing, e.g., the left ventricle wall).

The present invention is however applicable to other types of leads, for example, those leads having a distal electrode that remains on the surface of the wall of the patient's tissue to be detected/stimulated, and which are then provided with anchoring tines to maintain them in place at the chosen site. EP 0784993A1 (and its counterpart U.S. Pat. No. 5,800,499) and EP0779080A1 (all assigned to Sorin CRM S.A.S., previously known as ELA Medical) describe examples of such tined leads, which are incorporated herein by reference.

MRI examinations are presently contraindicated for patients with an implanted pacemaker or defibrillator. This is because of several problems caused by MRI:

Heating close to the electrodes of the lead connected to the generator;

Attraction forces and torques exerted on the device while immersed in the very high static magnetic field of the MRI device; and Unpredictable behavior of the device itself, due to exposure to these extreme magnetic fields.

The present invention aims to solve the first problem type. The heating problem appears especially in the vicinity of electrodes mounted at the distal end of the leads. Indeed, leads placed in the MRI imager act like antennas and pick up the radio frequency field (RF) emitted by the imager. Induced currents circulate in the conductors of the leads immersed in the RF field, causing heating of electrodes in contact with the blood and consequently heating of surrounding tissue. The heating at the electrodes is proportional to the density of current flowing therein and the smaller the surface of the electrode (the typical case being the surface of an active screw), the higher the current density and therefore the greater the heating of the surrounding tissue.

In practice, depending on the configuration of the generator, the leads and the MRI imaging, the temperature rise observed experimentally typically ranges from 8° C. (carbon electrodes) to 12° C. (metal electrodes), and sometimes even up to 30° C.

But the temperature increase should not exceed what is specified in the industry standard EN 45502-1 and its derivatives, which is less than 2° C. Indeed, an increase of 4° C. can cause a local cell death that has an immediate effect, among others, to substantially and irreversibly change the detection and stimulation thresholds, or even lead to complete loss of capture of the patient's heart beat.

It is certainly possible, as described in particular in U.S. Pat. Publication No. 2003/0204217 A1 and U.S. Pat. Publication No. 2007/0255332 A1, to provide an "MRI" safety mode in which a protection circuit connects to ground all conductors to prevent the flow of parasitic induced currents exposed to an MRI field. But this approach prevents the device from remaining functional for the duration of the MRI examination, which may last several minutes. It is therefore highly desirable that the implanted device can continue to provide seamless detection of depolarization potentials and possible delivery of stimulation pulses to the myocardium during an MRI examination.

To reduce the induced currents without disconnecting (i.e., open circuiting) or connecting to ground (i.e., grounding) the conductors, various techniques have been proposed, based primarily on putting in series with the conductor an impedance opposing current flow in an MRI examination situation. It may be a single coil (see, e.g., U.S. Pat. No. 7,123,013 B2), or a resonant tank circuit tuned to the RF frequency of the imager (see, e.g., U.S. Pat. Publication No. 2011/0106231, U.S. Pat. Publication No. 2010/0208397 A1 and U.S. Pat. Publication No. 2011/0054582 A1).

A passive protection circuit consisting in placing a PIN diode in parallel with a resistor in series with the electrode also has been proposed (cf. U.S. Pat. Publication No. 2008/0154348 A1). Yet another approach, disclosed in EP 2198917 A1 and its counterpart U.S. Pat. Publication No. 2010/0160989 (both assigned to Sorin CRM S.A.S., previously known as ELA Medical) is, in the case of a bipolar lead, to disconnect one of the conductors from normal functioning and to connect it to the ground of the housing of the generator, so that this conductor can act as protection shielding for the other conductor, which remains functional.

These options have, however, a number of limitations, including:

The systems implementing the commutations for their activation require a magnetic field detector in the generator;

Passive protection tank circuits are calculated for a specific imager frequency;

Integrated protection circuits may require an additional conductor in the lead and, consequently, cannot be used with any generator without suitable hardware modification of its circuits;

The protection components, such as diodes, are likely to cause substantial loss of energy when delivering stimulation pulses from the generator to the electrodes;

The addition of an integrated protection circuit in the distal portion of the lead body can cause, when the device is immersed in a MRI field, the reflection of an RF voltage to the generator that must be filtered and dissipated;

The incorporation of a protection circuit for self-protection of the lead in all circumstances is extremely sensitive in terms of technology, given the physical constraints: e.g., external diameter is limited to 5 French (1 F=⅓ mm), a need for an internal lumen in the lead body, and limitation of the length of the rigid part in the lead head; and The continuing high cost of implementation of these technologies.

Another disadvantage is that the protection circuit itself may undergo a rise in temperature that is transmitted to the proximal electrode and thus to the tissue of the heart wall.

Thus, in the U.S. Pat. Publication No. 2011/0106231 A1 above, the resonant tank circuit, which blocks the current flow to the anchoring screw forming an active electrode, comprises an inductor housed in the lead head. When the assembly is placed in a MRI field at a frequency corresponding to that of the tank circuit, high current flows in the inductor and causes significant heating within the lead head. The document proposes to evacuate this heat to the outside by equipping the lead head with a liner in the outer region of the inductance, forming a heat radiator. The heat produced in the inductance is then distributed radially in the lead head and then through the liner, to transfer the heat to the surrounding blood flow.

It is emphasized that in this structure the thermal diffuser is placed in line with the inductor (that is to say at about the middle of the terminal part of the lead head), and that the distal end of the lead is not affected by the thermal diffuser. Specifically, the distal end is made of a flexible material such as silicone which limits the contact pressure on the tissues. Silicone is a poor conductor of heat, but this is not a problem because in the presence of an RF field the screw is no longer powered (due to the tank circuit) and the tissues are not warming up at this level.

It should be understood that the structure described in this document requires the presence of a relatively large inductance, and electrical isolation between the inductor (which is connected in series with the stimulation conductor) and the thermal diffuser (which is necessarily in contact with the surrounding blood medium). All these constraints increase the complexity of implementation and the overall volume of the lead head.

U.S. Publication No. 2010/0208397 A1 and U.S. Pat. Publication No. 2011/0054582 A1 described above, disclose comparable lead head configurations, with a tank circuit to prevent against the harmful effects of an MRI field, and a heat diffuser arranged in line with the inductance of the tank circuit, so as to allow transfer of the heat generated in the inductor in the radial direction to the surrounding blood medium.

OBJECT AND SUMMARY

It is therefore an object of the present invention to provide a new lead configuration having a permanent "auto-protection" of the lead against the deleterious thermal effects of MRI fields without use of any protection circuitry or additional electronic component.

It is another object of the present invention to provide a screw lead configuration that, in all circumstances, significantly reduces the temperature rise at the distal end of the lead during exposure to an MRI field and avoids the partial or total destruction of tissue around the anchoring screw.

The starting point of the present invention is the discovery that the anchoring screw and its deployment system (in the case of a retractable screw) are encapsulated in a mechanism whose outer walls are electrically insulated, made of a material such as polycarbonate, polyurethane, silicone or polyetheretherketone ("PEEK"). One common element in all these materials is their low thermal conductivity. The mechanism containing the screw and its activation system, generally referred to as the "housing", is not only an electrical insulator (which is essential) but also a thermal insulator. The result is that in case of heating, the heat flow is confined to the center of the screw, with little opportunity to spread (diffuse) outward.

Indeed, the heat exchange between this zone and the adjacent volumes are limited:

On the distal side (i.e., at the tip of the screw) and on the radial side (i.e., on the periphery of the tip of the screw), the low thermal conductivity of muscle tissue in which the screw is implanted, and On the proximal side (i.e., at the side of the housing in contact with the cardiac wall, but outside thereof), by the effect of a "thermal cap" attributable to the low conductivity of the material of the housing.

Thus, upon heating of the screw under the effect of an intense MRI field, the temperature rise is even more pronounced when it is not possible to transfer the heat generated to the outside: neither to the mass of the myocardial wall (due to low thermal conductivity) or to the surrounding blood flow (due to the screening caused by the thermal cap effect of the housing enclosing the screw and deployment mechanism).

The present invention seeks to solve these problems by providing the end of the lead, on the housing enclosing the anchoring screw and its deployment mechanism, with an improved heat sink, preferably one as continuous a mass as possible, between the outer surface of the housing and the core of the screw anchored in muscle tissue (wherein the localized heating occurs), in order to utilize the heat dissipation effect generated by the blood flow around the housing of the lead head. The heat flow generated at the screw is then mainly dissipated in the proximal direction, into the blood stream via the thermally conductive housing, thus limiting the rise in temperature at the tissue level.

Broadly, the present invention is directed to a lead for intracardiac stimulation or defibrillation, known, for example, from U.S. Pat. Publication No. 2011/0106231 A1 mentioned above, which is incorporated herein by reference, comprising a tubular flexible sheath terminated at its distal end by a lead head, the lead head comprising an at least partially electrically insulating tubular outer housing, a means for anchoring the lead head, connected to the tubular housing, a distal stimulation electrode, arranged at the end of the lead head, and a heat sink member, the heat sink member being electrically isolated and carried by the tubular housing in an outer region thereof and comprising a solid part made of a thermally conductive material.

In one embodiment, the solid part of the heat sink element extends in the axial direction to the distal end of the lead head, and is terminated by a contact end face adapted to come into contact with a wall of a muscle of the patient to form a thermal bridge for heat transfer between this wall and the solid part.

In a preferred embodiment, the lead is a screw lead, and the means for anchoring comprises a projecting helical anchoring screw extending axially along the tubular housing. More preferably, the screw is an active screw electrically conductive on at least one end portion, forming said stimulation electrode. In this latter case, it may be advantageous to provide the screw with a spiral element, made of a thermally conductive material, inserted between the turns of the helical anchoring screw so as to fill the space existing between these turns.

The present invention is also applicable to leads wherein the means for anchoring includes one or more tines radially projecting to the outside of the tubular housing, and the stimulation electrode is a distal electrode to be supported against a muscle wall.

In a preferred embodiment, advantageously, the front face of the distal electrode contact is a radial plane face forming the distal end of the tubular housing.

In a lead configuration in which the outer housing comprises a tubular inner housing to a proximal end of the means for anchoring, preferably the solid part of the heat sink element extends in the radial direction with a heat transfer continuity solution from the housing to the outer free wall of the housing. In a preferred embodiment, it is advantageous to provide a thermally conductive material filling the cavity, such as a gel, including rehydratable hydrogel.

In one embodiment, the thermally conductive material of the solid part typically has a thermal conductivity of at least 5 W/mK.

In one embodiment, the thermally conductive material of the solid part is preferably a radio-transparent material. It can in particular be a metallic material such as titanium or a titanium alloy.

In one embodiment, the solid part has on its surface an electrically insulating coating, preferably a thermally conductive material, such as a diamond deposition.

In the case of a screw lead, the screw also may be provided on a part of its length an electrically insulating coating of a thermally conductive material, such as a diamond deposition.

DRAWINGS

Further features, characteristics and advantages of the present invention will become apparent to a person of ordinary skill in the art from the following detailed description of preferred embodiments of the present invention, made with reference to the accompanying drawings, in which like reference characters refer to like elements, and in which:

FIG. 1 illustrates the head of a lead of the present invention, in longitudinal section through an axial plane; and.

FIG. 2 is an enlarged view of the right side of FIG. 1, showing the method for the heat transfer within the distal end of the lead in contact with the heart wall.

DETAILED DESCRIPTION

With reference to the drawings FIGS. 1-2, embodiments of devices in accordance with the present invention will now be described.

With reference to FIG. 1, a lead head 10 of a retractable screw lead illustrated in a situation with the anchoring screw 20 in the deployed or extended position, anchored in the tissues of the heart wall. Lead head 10 is mounted at the end of a sheath 12 with which it constitutes the lead body. Sheath 12 has the form of a flexible hollow tube incorporating two (or more) electrical conductors 14, 16, connected to respective electrodes. Conductor 14 is connected to a proximal ring electrode 18, and conductor 16 is connected to anchoring screw 20, by means of a mobile body 22 having at its proximal end a tail 24 that is electrically and mechanically connected to conductor 16 so as to ensure electrical continuity from conductor 16 to screw 20 located at the distal end.

Lead head 10 also includes a mechanism (not shown in detail) for deployment of screw 20 so that, when deployed, screw 20 can be anchored in wall 26 of the endocardium, to ensure a mechanical connection with the myocardial tissue and prevent the displacement or dislodgement of lead head 10 once it is anchored in place. Screw 20 is in this embodiment an "active screw" meaning that it is electrically conductive and acts as the distal sensing/pacing (also called detection/stimulation) electrode by its connection to the generator via conductor 16.

Screw 20 and its deployment mechanism are housed in a rigid element 28 of lead head 10, generally referred to as a "housing" or a "can", of tubular shape.

To increase the efficiency of the screw, the latter is made conductive on the end portion of its distal end in the vicinity of the tip, with a reduced contact surface, typically of the order of 2 mm$^2$.

During an MRI exposure, the RF waves sensed by the lead body create a current flow that in turn causes a temperature rise at the distal end, particularly in the region 30 in the center of the conductive portion of the distal end of screw 20. Given the reduced contact surface, the current density at this location is particularly high, causing significant local heating of tissues which, if prolonged, may result in partial or total destruction of cells, as explained above. This heating is symbolized by the dashed lines 32 of the central region 30 of the screw.

The present invention proposes to diffuse and remove the heat thus generated, by providing the housing 28, at least in its most distal part, with a solid part 34 made of a thermally conductive material, so as to transfer (i.e., thermally conduct) to the proximal region the heat generated in region 30, to diffuse the heat in the distal area indicated by the region outlined 36 and to discharge it into the blood flow (volume 38) surrounding solid part 34.

It should be understood that solid part 34 is a unitary member constituting the case or housing of the distal region of the lead, with a thermal continuity solution between the muscle contact face 44 and the cylindrical outer surface immersed in the flow blood 38, or between the inner surface of the housing of the anchoring screw and the same cylindrical surface immersed in blood flow 38. It is indeed important that the heat transmission takes place in a way that is not interrupted by a thermal barrier material, whether made of air or an electrical insulator.

By transferring the heat away from region 30 where it arises, the temperature rise is limited in region 30 and in the surrounding myocardium tissue.

FIG. 2 is an enlarged view of the right side of FIG. 1, showing the method for the heat transfer within the distal end of the lead. In this figure, reference 44 designates the front end surface of solid part 34, which is preferably a circular flat surface coming in contact with wall 26 of the endocardium. The typical dimensions of the support surface are of the order of 5 to 7 French (1.66 to 2.33 mm) for the outside diameter OD and 1.2 to 2 mm for the inside diameter ID). The heat generated in region 30 at the center of the conductive portion of the distal end of screw 20 is transferred to solid part 34 via this contact face 44, which acts as a thermal bridge between the endocardium 26 and solid part 34.

The heat thus transfers essentially in the axial direction through the interface between contact face 44 and endocardium 26 (arrows 46), and in the mass of solid part 34 (arrows 48), which in turn transfers the heat to volume 38 and the surrounding blood flow (arrows 50).

The heat transfer from region 30 where the heat arises to the volume of blood flow 36 is also made by the intermediary of screw 20 itself, through the coils thereof that are in contact with the inner wall of cylindrical solid part 34 (arrows 52).

Thus, from the heat conduction point of view, solid part 34 is placed in communication with region 30 via two separate thermal bridges, (i) support surface 44 and (ii) anchoring screw 20.

To promote heat transfer through anchoring screw 20, it is advantageous to provide a thermally conductive spiral element 54 located between the turns of screw 20, so as to obtain a set with adjacent turns. This additional spiral element 54 has the function of filling the empty space between the turns of the screw 20 and thus to increase the mass of material capable of transferring heat to solid part 34. It may be made of titanium or, ideally, platinum (to benefit from the much higher thermal conductivity of that material).

Also advantageously, a thermal conductive gel may be introduced into the volume between anchoring screw 20 and the inner diameter of solid part 34 (e.g., the empty space referenced 56 in FIG. 2). The presence of such a thermally conductive gel eliminates any air which is highly resistant to heat transfer between the anchoring screw and the inner wall of solid part 34, in order to provide, here again, optimum heat transfer in the radial direction. The thermal conductive gel is preferably a particular hydrogel applied before implantation in a dry form, such that it instantly rehydrates on contact with water or blood. The hydrogel may be a particular polyvinylpyrrolidone (PVP) gel, which has, in the hydrated form, thermal characteristics near water (which is its main constituent, in this form). The other advantage of PVP gel is its well documented biocompatibility.

The choice of material for the thermally conductive solid portion 34 needs to take into account levels of typical thermal conductivity of different materials that may be encountered or used. This parameter is shown in Table 1 below for a variety of known materials.

TABLE 1

| Material | Thermal Conductivity (W/mK) |
|---|---|
| Air | 0.03 |
| Silicone | 0.11 |
| Parylene | 0.14 |
| PEEK | 0.25 |
| Blood | 0.50 |
| Muscle | 0.54 |
| Water | 0.60 |
| Carbon | 4 to 6 |
| Titanium | 7.50 |
| Stainless steel | 26.00 |
| Platinium | 71.60 |
| Diamond | 1000 to 2600 |

The materials normally used so far for producing housing 34 of the lead head, such as silicone, parylene, PEEK, all have a very low thermal conductivity, much less than 1, which produces an effect of preventing the thermal barrier diffusion of heat generated during an MRI at the active part of the screw tip.

To negate this thermal barrier effect, and replace it with a termally conductive pumping effect or heat sink, the invention proposes to select a material having a much higher thermal conductivity, typically at least about 5.

Given the biocompatibility constraints, it is possible to choose for solid part 34, in place of silicone or PEEK, a metal such as titanium, which has the advantage of being radiotransparent, and therefore preserves the functionality of other radiopaque markers enabling the surgeon to control the deployment of the screw under fluoroscopy. However, it is necessary to electrically insulate the outer surface of the solid part 34 made of titanium.

In this regard, it is known to isolate titanium parts by applying a coating of a material such as parylene, but the table above indicates that the thermal conductivity of this material is very low. To maintain the efficiency of the thermal bridge, therefore, the present invention proposes to replace the conventional parylene coating by a surface deposit of a material with high thermal conductivity, in particular by a diamond deposit. This material is particularly interesting in this application because it combines a very high thermal conductivity (1000-2600) and a satisfactory electrical isolation capacity. The deposit of a diamond coating on a metal cylinder is a technology in itself known, but it had so far been used mainly to benefit from the properties of very low friction coefficient of diamond, and thus facilitate sliding during introduction, but had never been proposed in the context of the present invention to take advantage of its exceptionally high thermal conductivity.

With reference to FIG. 1, insulating coating 40 illustrated as coating over the entire length of the solid part 34 with the possible exception of a region housing a collar 42 for steroid elution, near the area of contact with cardiac wall 26.

The diamond coating can be achieved not only on the solid and thermally conductive part of solid part 34 enclosing the screw 28 and its deployment mechanism, but also on the screw itself, except of course for an uncoated surface at the end of the tip to maintain the basic electrically conductive function of an active screw (substantially corresponding to the last two millimeters in the distal direction).

It should be understood that the reverse configuration is also possible, wherein the isolating diamond is deposited on the tip of the screw and the rest of the active screw is left uncoated. This configuration has the advantage of avoiding high current densities at the screw tip, which can locally cause a more intense heat, even more annoying in that it is poorly thermally transferred by the low conductive surfaces that a point presents. In fact, if the tip is isolated and the body of the screw is stripped, heat can be better distributed along the screw and also better transferred.

One skilled in the art will appreciate that the present invention can be practiced by embodiments other than those described herein, which are provided for purposes of illustration and explanation, and not of limitation.

The invention claimed is:

1. An intracardiac lead for stimulation or defibrillation, comprising a flexible tubular sheath having an axial direction and a distal end, and a lead head terminating the distal end, the lead head comprising:
    an at least partially electrically insulating tubular outer housing having an outer region;
    an anchor that anchors the lead head to a tissue of a patient, connected to the tubular housing, wherein the anchor extends axially from the distal end of the lead head,
    a distal stimulation electrode, disposed at the distal end of the lead head; and
    a heat sink comprising a solid part that is electrically isolated and carried by the tubular housing in an outer region thereof, wherein said solid part extends in the axial direction to the distal end of the lead head, and comprises a contact front face to be secured in contact with said tissue of the patient by said anchor extending therefrom, to form a thermal bridge between said tissue and said solid part.

2. The lead of claim 1, wherein the anchor comprises a projecting helical anchoring screw, said screw being an active screw that is electrically conductive on at least one end portion and comprises said distal stimulation electrode.

3. The lead of claim 2, further comprising a spiral element made of a thermally conductive material, inserted between the turns of the helical anchoring screw so as to fill the space existing between said turns.

4. The lead of claim 2, wherein the screw further comprises, on a part of its length, an electrically insulating coating of a thermally conductive material.

5. The lead of claim 4, wherein the electrically insulating coating of thermally conductive material in the screw portion is a diamond deposition.

6. The lead of claim 1, wherein the anchor comprises anchoring tines radially projecting to the outside of the tubular housing, and the distal stimulation electrode comprises a distal electrode to come in support against said tissue of a patient.

7. The lead of claim 1, wherein the contact front face further comprises a flat radial face forming the distal end of the tubular housing.

8. The lead of claim 1, wherein said flexible tubular sheath further comprises a radial direction and the tubular outer housing further comprises an inner housing for a proximal end of the anchor, and wherein said solid part of the heat sink extends in a radial direction with a heat transfer continuity solution from the housing to the free outer wall of the housing.

9. The lead of claim 8, wherein said tubular outer housing further comprises a cavity inside said inner housing and further comprising a thermally conductive material filling the cavity.

10. The lead of claim 9, wherein the thermally conductive material filling the cavity is a rehydratable hydrogel.

11. The lead of claim 1, wherein the thermally conductive materials of the solid part has a thermal conductivity of at least 5 W/mK.

12. The lead of claim 1, wherein the thermally conductive material of the solid part is a radio-transparent material.

13. The lead of claim 1, wherein the thermally conductive material of the solid part is a metallic material and the solid part includes an electrically insulating surface coating.

14. The lead of claim 13, wherein the metallic material is a titanium or a titanium alloy.

15. The lead of claim 13, wherein the electrically insulating coating is a thermally conductive material.

16. The lead of claim 15, wherein the electrically insulating coating of thermally conductive material of the solid part is a diamond deposition.

\* \* \* \* \*